United States Patent [19]

Kantor et al.

[11] Patent Number: 5,034,224
[45] Date of Patent: Jul. 23, 1991

[54] METHOD AND COMPOSITION FOR TREATING PROTOZOAL INFECTIONS

[75] Inventors: Sidney Kantor, Cranbury, N.J.; Robert L. Kennett, Jr., deceased, late of Lambertville, N.J., by Mary G. Kennett, executrix

[73] Assignee: American Cyanamid Company, Stamford, Conn.

[21] Appl. No.: 358,984

[22] Filed: May 30, 1989

[51] Int. Cl.$^5$ .................. A61K 35/74; A61K 31/44
[52] U.S. Cl. .................................... 424/122; 514/279
[58] Field of Search ..................... 424/122; 514/279

[56] References Cited

U.S. PATENT DOCUMENTS 4,148,882 4/1979 Celmer et al. ................. 424/122
4,278,663 7/1981 Liu et al. ....................... 424/119

Primary Examiner—Jerome D. Goldberg
Attorney, Agent, or Firm—John W. Hogan, Jr.

[57] ABSTRACT

This invention relates to a method and composition for the control of protozoal infections in warm-blooded animals by orally administering to said animals an effective amount of a new antibacterial produced in a microbiological fermentation under controlled conditions using a new subspecies of *Micromonospora citera* and mutants thereof. The antibacterial designated LL-E19085α is a highly effective anticoccidial agent especially useful for the prophylactic, pharmaceutical, and therapeutic treatment of poultry and other animals raised for meat production.

7 Claims, No Drawings

METHOD AND COMPOSITION FOR TREATING PROTOZOAL INFECTIONS

BACKGROUND OF THE INVENTION

Coccidiosis is an extremely severe disease which is of major concern to the meat-producing industry. This disease is caused by protozoan parasites which infect the host animals causing them to lose weight, reduce their feed efficiency and, in many instances, die. In poultry, these protozoan parasites are generally of the genus Eimeria; six species of which have been shown to be primary causative agents for the disease in poultry. These six species are: *Eimeria tenella, Eimeria necatrix, Eimeria mitis, Eimeria maxima, Eimeria brunetti,* and *Eimeria acervulina.*

Although coccidiosis has been recognized, for many years, as one of the most important diseases confronting the meat-producing industry, nevertheless, heretofore no entirely satisfactory method of control of the disease has been provided.

It is therefore, an object of this invention to provide a novel method for the control of protozoan infections in warm-blooded animals, particularly meat-producing animals such as poultry, swine, cattle, and sheep.

It is also an object of this invention to provide novel compositions effective for the control of protozoan infections in meat-producing animals and it is a further object of the invention to provide novel antibacterial compositions effective for controlling, treating, minimizing, preventing, ameliorating, or curing protozoal infections in warm-blooded animals, particularly in poultry and other meat-producing animals such as cattle, sheep, rabbits, and swine.

SUMMARY OF THE INVENTION

This invention relates to novel methods and compositions for controlling, treating, preventing or curing protozoal infections such as coccidiosis, malaria, sarcosporidiosis, cryptosporidiosis and toxoplasmosis in warm-blooded animals, particularly poultry and other meat-producing animals such as cattle, sheep and swine as well as companion animals such as dogs and cats. The method comprises orally administering to the animal a protozoacidally effective amount of LL-E19085α or pharmaceutically acceptable salts thereof.

While the structure of LL-E19085α has not yet been fully elucidated, it is proposed as follows:

DETAILED DESCRIPTION OF THE PREFERRED EMBODIMENTS

The physiochemical characteristics of LL-E19085α are as follows:

a. molecular formula: $C_{36}H_{31}NO_{12}$;
b. molecular weight: 669 FABMS;
c. elemental analysis: C, 64.55; H, 4.46; N, 1.92;
d. specific rotation $[\alpha]_D^{26} = -52°$ (C, 1.11% dichloromethane); e. ultra absorption spectra: λmax nm ε 0.1N HCL=224 nm (27,700), 225 nm (21,900), 328 nm (16,400), 420 nm (4,230);

λmax nm ε 0.1N NaOH=217 nm (76,10), 340 nm (15,100), 399 nm (12,900);

λmax nm ε $CH_3OH$=222 nm (38,200), 240 nm (30,100), 255 nm (30,100), 321 nm (24,500), 384 nm (8,050);

f. infrared absorption spectrum: (KBr disk), max ($cm^{-1}$) 1800, 1742, 1690, 1621, 1422, 1273;

g. proton magnetic resonance spectrum: ($CDCl_3$) with significant peaks as follows:

| δ | #H | M | J (Hz) |
|---|---|---|---|
| 13.47 | 1 | s | — |
| 8.20 | 1 | d | 8.5 |
| 7.92 | 1 | d | 8.5 |
| 7.58 | 1 | s | — |
| 7.19 | 1 | s | — |
| 7.09 | 1 | s | — |
| 4.78 | 1 | d | 11.6 |
| 4.45 | 1 | d | 11.6 |
| 4.02 | 3 | s | — |
| 3.99 | 3 | s | — |
| 3.48 | 1 | d | 12.8 |
| 3.35 | 1 | d | 12.8 |
| 2.21 | 2 | d | 6.8 |
| 2.10 | 1 | m | — |
| 1.83 | 3 | s | — |
| 1.80 | 3 | s | — |
| 0.955 | 6 | d | 6.48; | and h. a carbon-13 nuclear magnetic resonance spectrum: ($CDCl_3$) with significant peaks as follows:

| δ | M | δ | M | δ | M |
|---|---|---|---|---|---|
| 181.2 | s | 134.8 | s | 65.0 | t |
| 178.1 | s | 132.1 | d | 62.3 | s |
| 172.1* | s | 129.7 | s | 56.8 | q |
| 171.5 | s | 124.4 | d | 56.5 | q |
| 165.8 | s | 120.8 | s | 42.9 | t |
| 162.1 | s | 119.9 | s | 41.9 | t |
| 155.5 | s | 119.5 | s | 25.8 | q |
| 153.4 | s | 117.7 | d | 25.5 | d |
| 150.8 | s | 107.3 | s | 22.4 | q |

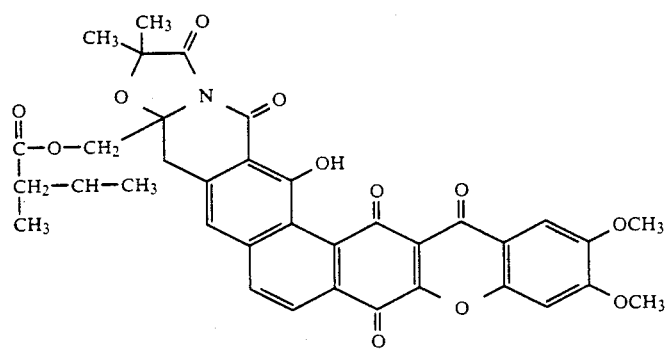

-continued

| δ | M | δ | M | δ | M |
|---|---|---|---|---|---|
| 148.7 | s | 104.9 | d | 22.3 | q |
| 140.7 | s | 100.4 | d | 20.2 | q |
| 137.7 | s | 93.4 | s | | |

*Two superimposed resonances.

In one preferred embodiment the present invention is a highly effective method for preventing, controlling or treating coccidiosis caused by Eimeria species in meat-producing animals, particularly chickens, turkeys, quail, pheasants, geese and ducks, but is likewise effective for controlling coccidiosis in other meat-producing animals by orally administering thereto an anticoccidially effective amount of the compound designated LL-E19085α or a mutant thereof. In practice, it is generally found that feed or drinking water containing from about 25 ppm to 1500 ppm and preferably 50 ppm to 1430 ppm of this compound LL-E18085α or pharmaceutically acceptable salt thereof is effective for controlling, preventing or eliminating, coccidiosis in animals consuming the treated feed or drinking water.

When the compounds of the invention are employed for the control of coccidiosis, the active compound is generally prepared as an animal feed premix or concentrate containing a relatively high percentage of the active ingredient. The premix or concentrate may then be blended with the animals daily ration or applied as a top dressing thereto.

Feed premixes or concentrates may be prepared by blending about 1.0% to 25%, and preferably about 5.0% to 15.0% by weight, of LL-E19085α or pharmaceutically acceptable salt of said anticoccidial or mutant thereof, or fermentation mash insolubles containing said antibacterial compound, with about 75% to 99.0% by weight of an edible carrier or diluent. Diluents suitable for use in preparation of said feed supplements and premixes include: corn meal, soybean meal, cotton seed oil meal, sodium chloride, bone meal, cane molasses, corn cob grits, rice hull meal, urea, and the like. The diluent helps to assure uniform distribution of the active ingredient throughout the finished feed into which it blended. Usually about one gram of premix is added per two kilograms of feed but larger or smaller amounts may be used, if desired.

Although administration of the compounds for controlling coccidiosis will generally be most practical when administered in or with the feed, or in the drinking water, the compounds of this invention may be administered to individual hosts in the form of pills, gels, boluses, tablets, drenches, capsules or the like. These latter types of administration are, of course, less practical than administration in or with the feed or drinking water, but can be utilized effectively for the treatment of a limited number of animals, particularly larger animals such as cattle, swine or sheep.

Since LL-E19085α is relatively insoluble in water, when administering said compound in water it will generally be most effective to first dissolve the active compound in a pharmaceutically acceptable organic solvent such as methanol, ethanol, acetone, DMSO, or the like, containing a suitable surfactant or dispersing agent, and then disperse the liquid composition in the drinking water of the animals being treated.

The new antibacterial agent LL-E19085α is produced by aerobic fermentation of microbial culture LL-E19085 which is a natural selection isolate of a culture isolated from a soil sample collected in Manyara, Tanzania. The culture was taxonomically characterized and identified as a new subspecies of Micromonospora citrea.

This new subspecies is maintained in the culture collection of the Medical Research Division, American Cyanamid Company, Pearl River, N. Y. as culture number LL-E19085. A viable culture of this new microorganism has been deposited with the ARS Culture Collection, Fermentation Laboratory, Northern Regional Research Center, U.S. Department of Agriculture, 1815 North University Street, Peoria, Ill. 61604 and has been added to its permanent collection. It has been assigned the strain designation NRRL 18351 by such depository.

Observations were made of the cultural, physiological and morphological features of culture LL-E19085 using methods well known in the art. The generic assignment of LL-E19085 to the genus Micromonospora was confirmed morphologically and chemically. The strain produced monospores on the vegetative hyphae. No aerial hyphae were observed. Electron microscopic examination showed that the spores were warty. Whole cell analysis showed that LL-E19085 containing the meso isomer as well as traces of the L isomer of diaminopimelic acid. This strain showed the presence of xylose plus traces of arabinose in its whole cell sugar hydrolysates. Therefor LL-E19085 is considered to be a subspecies of Micromonospora citrea.

Comparative data on the morphology of LL-E19085 is given in Tables I and II. Physiolocial data is given in Tables III and IV.

TABLE I

| ISP Agar Medium | Spores | Vegetative Mycelium | Soluble Pigments |
|---|---|---|---|
| Yeast-Malt (ISP 2) | Slight, black at edge | Strong orange (50) to medium orange-yellow (71*) | Slight, brown-black |
| Oatmeal (ISP 3) | None | Light orange-yellow (70) to vivid orange-yellow (66) | Slight, brownish |
| Inorganic Salts-Starch (ISP 4) | None | Light orange-yellow (70) to vivid orange-yellow (66) | Slight, brownish |
| Glycerol-Asparagine (ISP 5) (54) | Slight, brownish at edge | Light tone of brownish-orange | Slight, brownish |

*Parenthetical numbers are colors taken from Kelly, K. L. and Judd, D. B., Color. Universal Language and Dictionary of Names, Nat. Bur. Stand. (U.S.), Spec. Publ. 440, 1976, Washington, D.C. and the accompanying Inter-Society Color Council, National Bureau of Standards Centroid Color Charts.

TABLE II

| Agar Medium | Actinomycete Growth (28° C., 2 weeks) |
|---|---|
| Pablum | Brown vegetative hyphae. Sparse spores. Soluble dark brown pigment. |
| Yeast Czapek's | Brownish tan vegetative hyphae. Sparse spores. Slight soluble dark-brownish pigment. |
| Czapek's | Vegetative hyphae covered/spores. Black spores. Slight dark pigment. |
| Yeast Extract-Dextrose | Black spores. Dry soluble brownish pigment. |
| Nutrient | Orange-brown vegetative hyphae. Sparse spores. Intense brown-black pigment. |
| Bennett's Dextrin | Tan vegetative hyphae. Moderate black spores. Soluble reddish-brown pigment. |

TABLE II-continued

| Agar Medium | Actinomycete Growth (28° C., 2 weeks) |
|---|---|
| Glucose Asparagine | Orange-tan vegetative hyphae. No spores. Slight soluble dark pigment. |

TABLE III

| Carbohydrate | Carbohydrate Utilization |
|---|---|
| Arabinose | + |
| Cellulose | − |
| Fructose | ± |
| Glucose | + |
| Inositol | − |
| Mannitol | − |
| Raffinose | − |
| Rhamnose | − |
| Sucrose | ± |
| Xylose | + |

TABLE IV

| Gordon Test | Physiological Reaction |
|---|---|
| Hydrolysis of | |
| Casein | + |
| Xanthine | − |
| Hypoxanthine | − |
| Tyrosine | + |
| Adenine | + |
| Gelatin | + |
| Potato Starch | + |
| Esculin | + |
| Physiological Production of | |
| Nitrate Reductase | − |
| Phosphatase | + |
| Urease | − |
| Growth on | |
| Salicin | − |
| 5% Sodium Chloride | − |
| Lysozyme Broth | − |
| Decarboxylation of | |
| Acetate | + |
| Benzoate | − |
| Citrate | − |
| Lactate | + |
| Malate | − |
| Mucate | − |
| Oxalate | − |
| Propionate | + |
| Pyruvate | + |
| Succinate | − |
| Tartrate | − |
| Acid from | |
| Adonitol | − |
| Arabinose | + |
| Cellobiose | + |
| Dextrin | + |
| Dulcitol | − |
| Erythritol | − |
| Fructose | + |
| Galactose | + |
| Glucose | + |
| Glycerol | + |
| Inositol | − |
| Lactose | + |
| Maltose | + |
| Mannitol | − |
| Mannose | + |
| α-Methyl-D-glucoside | + |
| Melibiose | + |
| Raffinose | + |
| Salicin | − |
| Sorbitol | − |
| Sucrose | + |
| Trehalose | + |
| Xylose | + |
| β-Methyl-D-xyloside | − |
| Growth at | |
| 10° C. | − |
| 42° C. | + |
| 45° C. | + |

+ = positive;
− = negative

It is to be understood that for the production of the new antibacterial agent LL-E19085α, the present invention is not limited to this particular organism or to organisms fully answering the above growth and microscopic characteristics, which are given for illustrative purposes only. In fact it is desired and intended to include the use of mutants produced from this organism by various means such as exposure to x-radiation, ultraviolet radiation, N'-methyl-N-nitro-N-nitrosoguanidine, actinophages and the like, as well as the protozoacidal agents produced by these mutants.

Cultivation of *Micromonospora citrea* sp. LL-E19085 may be carried out in a wide variety of liquid culture media. Media which are useful for the production of antibiotic LL-E19085α include an assimilable source of carbon, such as starch, sugar, molasses, glycerol, etc.; an assimilable source of nitrogen, such as protein, protein hydrolysate, polypeptides, amino acids, cornsteep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the medium. Aeration is supplied by forcing sterile air through or onto the surface of the fermenting medium. Agitation is provided by a mechanical impeller. An antifoam agent may be added as needed. The growth of the organism is usually conducted at about 24°–37° C., preferably at about 28° C.

The invention in this application is further demonstrated by the examples set forth below.

EXAMPLE 1

Evaluation Of Test Compounds As Anticoccidial Agents

Evaluation of the effectiveness of compound LL-E19085α is determined in the following manner:
The poultry diet employed in the test is as follows:
Vitamin-amino acid premix: 0.5%
Trace minerals: 0.1%
Sodium chloride: 0.3%
Dicalcium phosphate: 1.2%
Ground limestone: 0.5%
Stabilized fat: 4.0%
Dehydrated alfalfa, 17% protein: 2.0%
Corn gluten meal, 41% protein: 5.0%
Menhaden fish meal, 60% protein: 5.0%
Soybean oil meal, 44% protein: 30.0%
Ground yellow corn, fine to: 100.0%

The vitamin-amino acid premix in the above feed composition is prepared from the following formulation. The expressions of quantity relate to the units per kilogram of the finished feed composition.
Butylated hydroxy toluene: 125.0 mg
dl-Methionine: 500.0 mg Vitamin A: 3300.0 I.U.
Vitamin $D_3$: 1100.0 I.C.U.
Riboflavin: 4.4 mg
Vitamin E: 2.2 I.U.
Niacin: 27.5 mg
Panthothenic acid: 8.8 mg
Choline chloride: 500.0 mg
Folic acid: 1.43 mg
Menadione sodium bisulfate: 1.1 mg
Vitamin $B_{12}$: 11.0 mcg
Ground yellow corn, fine: 5.0 gm A mixed inoculum of 5000 sporulated oocysts of *Eimeria acervulina* and a sufficient number of oocysts of *Eimeria tenella* to produce 85% to 100% mortality in untreated controls was given to one-day-old chicks, by direct inoculation into the crops of all chicks. The chicks were given free access to feed and water during the entire test period. Two days before inoculation, medicated feed with several levels of drug was presented to the various groups of chicks. Seven days after inoculation the tests were terminated and the birds were weighed, necropsied and their intestinal tracts examined for lesions. The results appear in Table V below. These results show that improved survival of infected chicks is obtained when 50 to 1430 ppm or less of antibiotics LL-E19085α is administered to infected chicks in their diet. These levels also show a significant suppression of lesions due to *Eimeria tenella* and *Eimeria acervulina*. These levels are also shown to provide significant improvement in weight gains in the treated birds.

TABLE V

Evaluation of Antibiotic LL-E19085alpha As An Anticoccidial Agent In Chicks

| Test No | Compound | Concentration in diet, ppm | No Birds Started | % Survival | % Birds with reduced lesions E. tenella | % Birds with reduced lesions E. acervulina | Relative weight gains untreated uninfected birds % ± controls |
|---|---|---|---|---|---|---|---|
| I | LL-E19085alpha | 50 | 5 | 80 | 0 | 100 | +28 |
|  | LL-E19085alpha | 100 | 5 | 100 | 0 | 100 | +47 |
|  | LL-E19085alpha | 200 | 5 | 60 | 20 | 100 | +65 |
| II | LL-E19085alpha | 340 | 5 | 100 | 0 | 0 | +30 |
| III | LL-E19085alpha | 360 | 5 | 100 | 0 | 60 | +30 |
|  | LL-E19085alpha | 715 | 5 | 100 | 60 | 100 | +51 |
|  | LL-E19085alpha | 1430 | 5 | 100 | 80 | 100 | +36 |

EXAMPLE 2

Inoculum Preparation

A typical medium used to grow the inocula was prepared according to the following formula:
Dextrose: 1.0%
Dextrin: 2.0%
Yeast extract: 0.5%
NZ Amine A *: 0.5%
Calcium carbonate: 0.1%
Defoam agent: 0.3%
Water qs: 100%
*A pancreatic digest of casein, registered trademark of Sheffield Chemical, Norwich, N.Y.

This medium was sterilized and a 100 mL portion in a 500 mL flask was inoculated with mycelial scrapings from an agar slant of the culture *Micromonospora citrea* sp LL-E19085. The inoculated flask was then placed on a rotary shaker and agitated vigorously for approximately 48 hours at 32° C., providing primary inoculum.

A 100 mL portion of this primary inoculum was then used to inoculate 10 liters of the above sterile medium which was incubated at 32° C. with aeration for 72 hours, providing secondary inoculum.

A 10 liter portion of this secondary inoculum was then used to inoculate 260 liters of the above sterile medium in a tank. This medium was incubated at 32° C. with agitation by an impeller driven at 180 rpm, a sterile air flow of 200 liters per minute and the addition of 50 mL of a defoaming agent for about 48 hours, providing tertiary inoculum.

EXAMPLE 3

Fermentation

A fermentation medium was prepared according to the following formulations:
Dextrin: 3.0%
Dextrose: 0.5%
Nutrisoy: 1.5%
Corn steep liquor: 0.5%
Calcium carbonate: 0.5%
Defoam agent: 0.3%
Water qs: 100%

A 2800 liter portion of the above medium in a tank was sterilized and then inoculated with 300 liters of tertiary inoculum prepared as described in Example 2. Aeration was supplied at the rate of 6.5 liters of sterile air per liter of mash per minute and agitation was supplied by an impeller driven at about 110 rpm. The temperature was maintained at 28° C. and defoaming agent was added as required. The fermentation was terminated after 129 hours.

EXAMPLE 4

Isolation Of Antibiotic LL-E19085α

A 1500 liter portion of the whole harvest mash, prepared as described in Example 3 was mixed with 15 liters of toluene for 30 minutes, then 250 lb of diatomaceous earth was added. After mixing for 15 minutes this mixture was filtered and the cake washed with 150 liters of water. The cake was slurried in a mixture of 208 liters of acetone, 416 liters of dichloromethane and 20 liters of 1.5N hydrochloric acid for 2 hours and then filtered. The cake was washed with about 175 liters of dichloromethane with the wash and filtrate combined. The cake was then washed with about 800 liters of water and this wash also combined with the above wash and filtrate and mixed. The dichloromethane layer was separated and washed with an equal volume of water. The dichloromethane layer was separated and concentrated to 100 liters, reextracted with fresh methylene chloride if any aqueous phase was present, and finally concentrated to about 1-3 liters.

The dichloromethane extracts were triturated repeatedly, first with hexane:dichloromethane (9:1) and then with hexane along to remove the bulk of the fatty impurities giving a brown powder.

Several such partially purified preparations, from fermentations conducted as described in Example 3, totaling 20 g and averaging 10–30% LL-E19085α, were combined and purified by reverse-phase chromatography. The column consisted of a 15 liter bed of $C_{18}$ bonded phase packing of 40 micron particle size. The charge was loaded onto the column in 500 mL of acetonitrile:tetrahydrofuran (1:1). The column was developed at a flow rate of 1.0 liter per minute with a mobile phase consisting of acetonitrile:0.1M pH 4.5 ammonium acetate buffer (8:2). Fractions were collected at approximately 12 minute intervals. Fractions 6 and 7 were combined and evaporated, giving 2.7 g of pure LL-E19085α having the characteristics disclosed in the hereinabove specification.

We claim:

1. A method for the control of protozoan infections in infected warm-blooded animals which comprises orally administering to said warm-blooded animals a protozoacidally effective amount of a protozoacidal agent LL-E19085α or a pharmaceutically acceptable salt thereof, said LL-E19085α having a. molecular formula: $C_{36}H_{31}NO_{12}$;
   b. molecular weight: 669 FABMS;
   c. elemental analysis: C, 64.55; H, 4.46; N, 1.92;
   d. specific rotation $[\alpha]_D^{26} = -52°$ (C, 1.11% dichloromethane);
   e. ultra absorption spectra: λmax nm ε 0.1N HCL = 224 nm (27,700), 255 nm (21,900), 328 nm (16,400), 420 nm (4,230); λmax nm ε 0.1N NaOH = 217 nm (76,10), 340 nm (15,100), 399 nm (12,900); λmax nm ε $CH_3OH$ = 222 nm (38,200), 240 nm (30,100), 255 nm (30,100), 321 nm (24,500), 384 nm (8,050);
   f. infrared absorption spectrum: (KBr disk), max ($cm^{-1}$) 1800, 1742, 1690, 1621, 1422, 1273;
   g. proton magnetic resonance spectrum: ($CDCl_3$) with significant peaks as follows:

| δ | #H | M | J (Hz) |
|---|---|---|---|
| 13.47 | 1 | s | — |
| 8.20 | 1 | d | 8.5 |
| 7.92 | 1 | d | 8.5 |
| 7.58 | 1 | s | — |
| 7.19 | 1 | s | — |
| 7.09 | 1 | s | — |
| 4.78 | 1 | d | 11.6 |
| 4.45 | 1 | d | 11.6 |
| 4.02 | 3 | s | — |
| 3.99 | 3 | s | — |
| 3.48 | 1 | d | 12.8 |
| 3.35 | 1 | d | 12.8 |
| 2.21 | 2 | d | 6.8 |
| 2.10 | 1 | m | — |
| 1.83 | 3 | s | — |
| 1.80 | 3 | s | — |
| 0.955 | 6 | d | 6.48; | and h. a carbon-13 nuclear magnetic resonance spectrum: ($CDCl_3$) with significant peaks as follows:

| δ | M | δ | M | δ | M |
|---|---|---|---|---|---|
| 181.2 | s | 134.8 | s | 65.0 | t |
| 178.1 | s | 132.1 | d | 62.3 | s |
| 172.1* | s | 129.7 | s | 56.8 | q |
| 171.5 | s | 124.4 | d | 56.5 | q |
| 165.8 | s | 120.8 | s | 42.9 | t |
| 162.1 | s | 119.9 | s | 41.9 | t |
| 155.5 | s | 119.5 | s | 25.8 | q |
| 153.4 | s | 117.7 | d | 25.5 | d |
| 150.8 | s | 107.3 | s | 22.4 | q |
| 148.7 | s | 104.9 | d | 22.3 | q |
| 140.7 | s | 100.4 | d | 20.2 | q |
| 137.7 | s | 93.4 | s | | |

*Two superimposed resonances.

2. The method according to claim 1 wherein said warm-blooded animals are meat-producing animals or companion animals.

3. The method according to claim 2 wherein the warm-blooded animals are meat-producing animals, the protozoan infection is coccidiosis and the protozoacidal agent is administered to the meat-producing animals in their feed or drinking water in an amount from about 25 ppm to 1500 ppm.

4. The method according to claim 3 wherein the meat-producing animals are poultry and the protozoacidal agent is administered in the feed or drinking water in an amount from about 50 ppm to 1430 ppm.

5. An animal feed premix composition useful for the control of coccidiosis infections in meat-producing animals comprising about 75% to 99% by weight of a solid edible diluent and about 1% to 25% by weight of the anticoccidial agent LL-E19085α as defined in claim 1 or pharmaceutically acceptable salts.

6. The composition according to claim 5 for the control of coccidiosis infections in poultry, swine, cattle or sheep, wherein the solid diluent is an animal feed.

7. An animal feed composition for the control of coccidiosis in poultry comprising a solid edible poultry feed containing about 25 ppm to 1500 ppm of the anticoccidial agent LL-E19085α as defined in claim 1.

* * * * *